United States Patent [19]

George et al.

[11] Patent Number: 5,164,397

[45] Date of Patent: Nov. 17, 1992

[54] 2-AMINOPYRIMIDINE-4-CARBOXAMIDE DERIVATIVES, THEIR PREPARATION AND THEIR APPLICATION IN URINARY THERAPEUTICS

[75] Inventors: Pascal George, St. Arnoult-en-Yvelines; Philippe Manoury, Verrières-le-Buisson; Jacques Froissant, Morée; Jean-Pierre Merly, Sceaux, all of France

[73] Assignee: Synthelabo, Paris, France

[21] Appl. No.: 634,469

[22] Filed: Dec. 27, 1990

[30] Foreign Application Priority Data

Dec. 28, 1989 [FR] France ................. 89 17304

[51] Int. Cl.$^5$ ................. C07D 247/02; C07D 295/13; A61K 31/505
[52] U.S. Cl. ................. 514/275; 544/295; 544/392; 544/402
[58] Field of Search ................. 514/275; 544/295

[56] References Cited
FOREIGN PATENT DOCUMENTS
2139083  2/1973  Fed. Rep. of Germany .

OTHER PUBLICATIONS
Gilchrist, "Hetereocyclic Chemistry" (1985) pp. 303-321.

*Primary Examiner*—Mark L. Berch
*Attorney, Agent, or Firm*—Jacobson, Price, Holman & Stern

[57] ABSTRACT

A compound of formula (I)

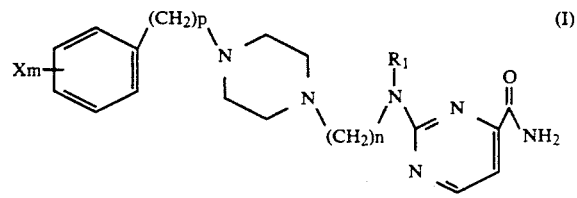

in which
n denotes 2, 3, 4, or 5,
p denotes 0 or 1,
m denotes 0, 1, 2, 3, 4, or 5, and
$R_1$ denotes a hydrogen atom or a methyl group,
each X, which may be identical or different to any other X if m is greater than 1, denotes fluorine, chlorine, methoxy, isopropyl or cyclopropyl,
in the form of a free base or an acid addition salt.

10 Claims, No Drawings

2-AMINOPYRIMIDINE-4-CARBOXAMIDE DERIVATIVES, THEIR PREPARATION AND THEIR APPLICATION IN URINARY THERAPEUTICS

The present invention relates to 2-amino-pyrimidine-4-carboxamide derivatives, to their preparation and to their application in therapeutics.

The present invention provides a compound of formula (I)

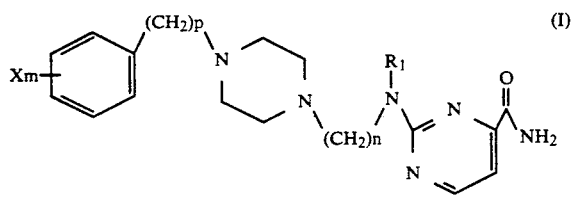

in which:
n denotes 2, 3, 4 or 5,
p denotes 0 or 1,
$R_1$ denotes a hydrogen atom or a methyl group,
m denotes 1, 2, 3, 4 or 5, and
each X, which may be identical or different to any other x if m is greater than 1, denotes fluorine, chlorine, methoxy, isopropyl or cyclopropyl,
in the form of a free base or an acid addition salt.

Preferred compounds are those which satisfy one or more of the following conditions:
n denotes 2 or 3;
p denotes 0;
m denotes 0, 1 or 2; and
the salt is fumarate, fumarate hemihydrate; hemifumarate; difumarate or dihydrochloride.

The substituent(s) X may be at any position of the aryl ring.

The compound of formula (I) may be prepared according to the process illustrated by scheme 1 below.

An optionally substituted piperazine of formula (II) (in which m, p and X are defined above) is reacted with a halogenated reactant of formula (III) (in which Y denotes a halogen atom, n is as defined above and either $R_1$ is as defined above and R denotes an amine-protecting group, for example a triphenylmethyl group, or $R_1$ and R together form a protecting group such as the phthalimide group, for example in a similar manner to that described in J. Med. Chem. (1988), 31(10), 1968-1971, J. Med. Chem., (1989), 32(8), 1921-1926, and Chem. Pharm. Bull. (1989), 37(1), 100-105).

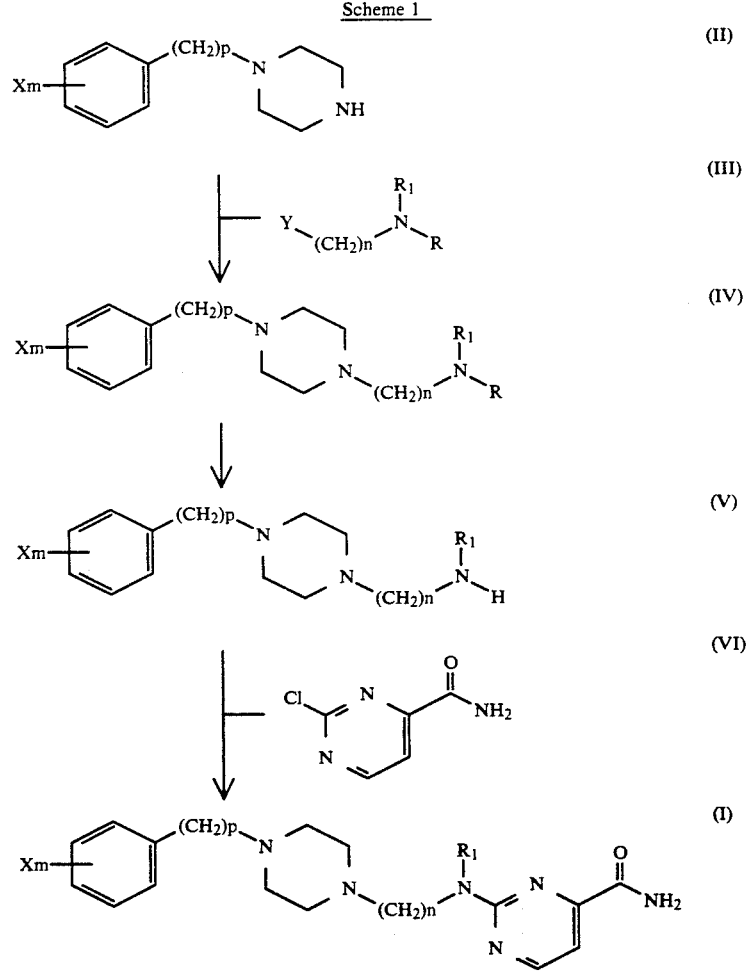

Scheme 1

The reaction is carried out in an aprotic solvent such as dimethylformamide, in the presence of a base, for example an organic base such a triethylamine or an inorganic base such as potassium carbonate, at a temperature of 40° to 80° C.

A piperazine of formula (IV) is obtained, whose end alkylamine is then deprotected; in the case where R is an amine protecting group such as the triphenylmethyl group, with gaseous hydrochloric acid in an aliphatic alcohol, for example methanol, at a temperature of 0° to 60° C., especially 0° to 40° C.; and, in the case where R and $R_1$ together form a protecting group such as a phthalimide group, a treatment is carried out which is similar to that described in the literature cited above, for example with hydrazine.

The amine of formula (V) is thus obtained, and this is reacted with 2-chloropyrimidine-4-carboxamide of formula (VI) in an aprotic solvent, for example dimethylformamide, in the presence of a base, for example potassium carbonate, at a temperature of 20° to 80° C., especially 20° C. to 40° C., to give a 2-aminopyrimidine-4-carboxamide derivative of formula (I). The compound of formula (I) is, if desired, converted into an acid addition salt.

Some compounds of formula (V) in which p=0 are described in DE-2,143,730, DE-2,314,114, DE-3,524,635, U.S. Pat. No. 3,398,151 and U.S. Pat. No. 4,748,240.

The halogenated reactant of formula (III) is either available commercially when $R_1$ and R together form a phthalimido group or, when $R_1$ is H or $CH_3$, can be prepared according to scheme 2, given below, and according to which an -haloalkylamine of formula (VII) is reacted with a compound of formula RCl, in this case trityl chloride, in an inert halogenated solvent such as dichloromethane in the presence of an organic base such as triethylamine, at a temperature of 20° to 80° C.

The 2-chloropyrimidine-4-carboxamide of formula (VI) can be prepared according to scheme 3, given below, from 2-chloropyrimidine-4-carbonitrile of formula (VIII), by treatment with gaseous hydrochloric acid in formic acid. 2- Chloropyrimidine-4-carbonitrile is prepared according to the method described in J. Het. Chem. (1964), 1, 130–133.

The following Examples further illustrate in detail the preparation of some compounds according to the invention. The numbers shown in brackets in the titles of the Examples correspond to those of the Table given later.

Elemental microanalyses and IR and NMR spectra confirm the structures of the products obtained.

Scheme 2

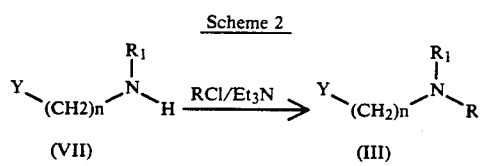

Scheme 3

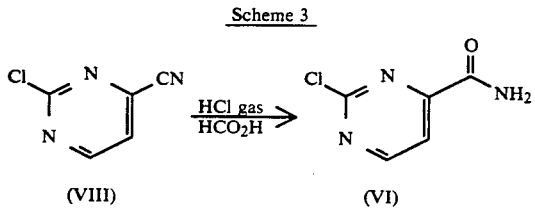

EXAMPLE 1

(Compound No. 5)

2-[[3-[4-(5-chloro-2-methoxyphenyl)piperazin-1-yl]propyl]amino]pyrimidine-4-carboxamide fumarate a) 2-Bromo-N-(triphenylmethyl)ethanamine 272.1 g (976 mmol) of triphenylchloromethane, 800 ml of dichloromethane and 200 g (976 mmol) of 2-bromoethanamine hydrobromide are introduced into a 2-1 round bottom flask placed under nitrogen. The mixture is stirred and 300 ml of triethylamine are added dropwise and stirring is continued for 48 h. The triethylamine hydrochloride which precipitates is separated off, water is added to the filtrate, the organic phase is separated off and is washed with water and dried over sodium sulphate, and the solvent is evaporated off. An oil is obtained, which is purified by chromatography on a column of silica gel. After recrystallisation from a mixture of dichloromethane and cyclohexane 273.17 g of white solid are obtained. Melting point: 108°–109° C.

b) 2-[4-(2-Methoxyphenyl)piperazin-1-yl]-N-(triphenylmethyl)ethanamine 10 g (27.3 mmol) of 2-bromo-N-triphenylmethyl)ethanamine, 200 ml of acetonitrile, 5.15 g (27.3 mmol) of 1-(2-methoxyphenyl)piperazine, 5.6 g of anhydrous potassium carbonate, a few particles of sodium iodide and 1 ml of dimethylformamide are introduced into a 500-ml round bottom flask fitted with a condenser and placed under nitrogen. The mixture is heated under reflux for 15 h, the solvents are evaporated off, water and dichloromethane are added, the organic phase is separated off and is washed with water and dried over sodium sulphate and the solvent is stripped off. A viscous oil is obtained, which is purified by chromatography on a column of silica gel by eluting with a mixture of ethyl acetate and dichloromethane. 9.24 g of product are isolated.

c) 2-[4-(2-Methoxyphenyl)piperazin-1-yl]ethanamine trihydrochloride 400 ml of methanol are added to the preceding compound and, after homogenisation, gaseous hydrochloric acid is bubbled through the solution for 10 min. The precipitate formed is filtered off, is rinsed with methanol and is dried under vacuum. 5.33 g of white solid are obtained.

d) 2-[[2-[4-(2-Methoxyphenyl)piperazin-1-yl]ethyl]amino]-pyrimidine-4-carboxamide fumarate 5.33 g (15.36 mmol) of 2-[4-(2-methoxyphenyl)piperazin-1-yl]ethanamine trihydrochloride, 2.44 g (15.36 mmol) of 2-chloro-pyrimidine-4-carboxamide, 200 ml of acetonitrile and 12 ml of triethylamine are introduced into a 500-ml round bottom flask fitted with a condenser and placed under nitrogen. The mixture is heated under reflux for 12 h, is allowed to cool, the solvent is evaporated off, water and dichloromethane are added to the residue, the organic phase is separated off and is washed with water and dried over sodium sulphate, the solvent is evaporated off, the residue is taken up with ethyl acetate, an impurity is separated off by filtration and the filtrate is evaporated down. 1.86 g of solid are obtained. Melting point: 185°–187° C. (decomposition).

1.85 g (5.19 mmol) of the above are introduced into a 1—1 round bottom flask, 0.602 g (5.19 mmol) of fumaric acid are added and the whole is dissolved using hot methanol. The solution is filtered, is concentrated and is allowed to cool. The precipitate is filtered off, is recrystallised from methanol and is dried under vacuum. 1.58 g of fumarate are finally isolated.

Melting point: 224°–225° C.

EXAMPLE 2

(Compound NO. 11)

2-[[2-[4-(2-Cyclopropylphenyl)piperazin-1-yl]ethyl]methylamino]pyrimidine-4-carboxamide fumarate a) 2-Chloro-N-methyl-N-(triphenylmethyl)-ethanamine 138.95 g (1.85 mol) of 2-(methylamino)ethanol and 500 ml of dichloromethane are introduced into a 2-l round bottom flask and gaseous hydrochloric acid is bubbled through for two 5-min periods with an interval of 30 min. The solution is partially concentrated and 145 ml (1.98 mol) of thionyl chloride are then added slowly over 1 h 30 min. The mixture is stirred at room temperature for 10 h and is then heated to 50° C. for 2 h. It is allowed to cool, the solvent is evaporated off and the residue is taken up twice with toluene, which is evaporated off. The residue is rinsed with a mixture of diethyl ether and pentane and is dried under vacuum in the presence of phosphorus pentoxide. 230.18 g of 2-chloro-N-methylethanamine hydrochloride are obtained. 46.17 g (355.1 mmol) of this are placed in a 1—1 round bottom flask placed under nitrogen and fitted with a dropping funnel, 100 g (358.7 mmol) of triphenylchloromethane and 400 ml of dichloromethane are added, and 100 ml of triethylamine are introduced slowly. Stirring is continued for 2 days, then water is added, the organic phase is separated off, is washed with water and dried over sodium sulphate and the solvent is evaporated off. The residue is purified by chromatography on a column of silica gel by eluting with a mixture of dichloromethane and cyclohexane and, after recrystallisation from cyclohexane, 79 g of compound are obtained.

Melting point: 161°–163° C.

b) 2-[4-(2-Cyclopropylphenyl)piperazin-1-yl]-N-methylethanamine trihydrochloride 9.0 g (44.4 mmol) of 1-(2-cyclopropylphenyl)piperazine, 200 ml of dimethylformamide, 15 g (44.4 mmol) of 2-chloro-N-methyl-N-(triphenylmethyl)-ethanamine and 9 g of potassium carbonate are introduced into a 500-ml round bottom flask fitted with a condenser and placed under nitrogen and the mixture is heated to 96° C. for 6 h three times. The solvent is evaporated off, the residue is taken up with water and dichloromethane, the organic phase is separated off, is washed with water and is dried over sodium sulphate and the solvent is stripped off. 4.17 g of 2-[4-(2-cyclopropylphenyl)piperazin-1-yl]-N-methyl-N-(triphenylmethyl)ethanamine are obtained in the form of oil, which is dissolved in 200 ml of methanol, gaseous hydrochloric acid is bubbled through it for 10 min, the mixture is concentrated, is allowed to stand for 2 days and the precipitate is separated off by filtration. 2.94 g of compound are obtained.

c) 2-[[2-[4-(2-Cyclopropylphenyl)piperazin-1-yl]ethyl]methylamino]pyrimidine-4-carboxamide fumarate 2.7 g (7.31 mmol) of 2-[4-(2-cyclopropylphenyl)piperazin-1-yl]-N-methylethanamine trihydrochloride, 1.15 g (7.31 mmol) of 2-chloropyrimidine-4-carboxamide, 8 g of potassium carbonate and 200 ml of acetonitrile are introduced into a 500-ml round bottom flask fitted with a condenser and placed under nitrogen and the mixture is heated under reflux for 12 h. It is allowed to cool, the solvent is evaporated off, the residue is taken up with water and dichloromethane, the organic phase is separated off, is washed with water and is dried over sodium sulphate, the solvent is evaporated off and the residue is purified by chromatography on a column of silica gel. After recrystallisation 2.223 g of compound are obtained in the form of free base.

Melting point: 162.5°–163.5° C.

Its fumarate is prepared by adding 0.678 g (5.84 mmol) of fumaric acid and then methanol at 80° C. until dissolved, the mixture is filtered, is concentrated and is allowed to cool. The precipitate is isolated by filtration, is rinsed with methanol and then with diethyl ether, and is recrystallised from methanol. 1.67 g of fumarate are finally isolated.

Melting point: 177°–180° C.

EXAMPLE 3

(Compound No. 14)

2-[[3-[4-(3-Chlorophenyl)piperazin-1-yl]propyl]amino]pyrimidine-4-carboxamide fumarate a) 2-Chloropyrimidine-4-carboxamide 338 g of 98% strength formic acid are introduced into a 1—1 round bottom flask fitted with magnetic stirring and containing 131.9 g (946 mmol) of 2-chloropyrimidine-4-carbonitrile, and a stream of gaseous hydrochloric acid is passed through slowly for 1 h 30 min. The mixture is allowed to stand overnight, the solid is isolated on sintered glass and is then purified by recrystallisation with filtration while hot, from a mixture of nitromethane and ethyl acetate. In this way, 107.03 g of grey solid are isolated as three crops, after drying under vacuum and with heating. Melting point: 152.5°–154° C.

b) 3-Bromo-N-(triphenylmethyl)propanamine 139.5 g (0.5 mol) of chlorotriphenylmethane in solution in 200 ml of dichloromethane are added to 153.3 g (0.7 mol) of 3-bromopropylamine hydrobromide in solution in 200 ml of dichloromethane. 132.0 g, that is 180.8 ml (1.3 mol) of triethylamine are then added slowly over a 3-h period. A whitish heterogeneous mixture is obtained, which is stirred for 14 h.

It is poured into water, the organic phase is separated off, is washed with water, is dried and the solvent is evaporated off, yielding 220.5 g of oily product. The residue is taken up with a 1/1 cyclohexane/toluene mixture and an insoluble material is separated off by decanting. The organic phase is reduced to half its volume and petroleum ether is added slowly. 111.2 g of white solid are obtained by wet grinding.

Melting point: 100°–102.5° C.

c)
3-[4-(3-Chlorophenyl)piperazin-1-yl]-N-(triphenylmethyl)propanamine

A mixture of 5.9 g (30 mmol) of 1-(3-chlorophenyl)-piperazine, 12.55 g (33 mmol) of 3-bromo-N-(triphenylmethyl)propanamine, 6.2 g (45 mmol) of potassium carbonate and 60 ml of dimethylformamide is stirred at 90° C. for 6.5 h under argon. The mixture is then poured into iced water and is extracted with ethyl acetate. The organic phase is separated off, is washed with water, is dried and the solvent is evaporated off. 15.7 g of oily residue are obtained and are purified by chromatography on a column of silica gel by eluting with a 99/1 dichloromethane/methanol mixture, which yields 11.8 g of light yellow oil.

d) 3-[4-(3-Chlorophenyl)piperazin-1-yl]propanamine

Gaseous hydrochloric acid is introduced for 10 min into a round bottom flask containing 11.2 g (22.6 mmol) of 3-[4-(3-chlorophenyl]piperazin-1-yl]-N-(triphenylmethyl)propanamine and 300 ml of methanol, while the mixture is cooled in a bath of iced water. The mixture is allowed to return to room temperature and is then heated under reflux for 5.5 h. The solution is reduced to half its volume and is allowed to cool. The solid which precipitates is filtered off, is treated with water and aqueous ammonia, the mixture is extracted with ethyl acetate, the organic phase is washed with water and is dried and the solvent is evaporated off. 3.9 g of light yellow oil are obtained.

e)
2-[[3-[4-(3-Chlorophenyl)piperazin-1-yl]propyl]amino]-pyrimidine-4-carboxamide fumarate 3.9 g (15.4 mmol) of 3-[4-(3-chlorophenyl)piperazin-1-yl]propanamine, 2.42 g (15.4 mmol) of 2-chloropyrimidine-4-carboxamide, 70 ml of dimethylformamide and a catalytic quantity of sodium iodide are introduced into a 100-ml round bottom flask, under argon atmosphere. 2.34 g (16.9 mmol) of potassium carbonate are added further and the mixture is stirred at room temperature for 19 h. The mixture is then treated with water and is extracted with ethyl acetate, the organic extract is washed with water and is dried and the solvent is evaporated off. An orange-coloured oil is obtained, which is ground wet in ethyl acetate. After filtration and drying, 2.2 g of white solid are isolated.

Its fumarate is prepared by dissolving it in 100 ml of ethanol and adding to it 0.68 g of fumaric acid dissolved in 100 ml of ethanol and then 100 ml of ethanol. The mixture is heated under reflux, the ethanol is evaporated off, the residual oil is ground wet in ethyl acetate and the solid obtained is recrystallised from ethanol. 2.3 g of fumarate are finally isolated.

Melting point: 187°–189° C.

EXAMPLE 4

(Compound No. 12).

2-[[3-[4-(2-Cyclopropylphenyl)piperazin-1-yl]propyl]-methylamino]pyrimidine-4-carboxamide a)
3-[4-(2-Cyclopropylphenyl)piperazin-l-yl]-N-methyl-propanamine

The operation is carried out similarly to that described in Example 2 (a and b), starting with 3-(methylamino)propanol.

b)
2-[[3-[4-(2-Cyclopropylphenyl)piperazin-1-yl]propyl]-methylamino]pyrimidine-4-carboxamide 1.25 g (4.09 mmol) of 3-[4-(2-cyclopropylphenyl)piperazin-1-yl]-N-methylpropanamine, 150 ml of acetonitrile, 0.645 g (4.09 mmol) of 2-chloropyrimidine-4-carboxamide and 1 g of potassium carbonate are introduced into a 250-ml round bottom flask fitted with a condenser and with a calcium chloride safety tube. The mixture is heated under reflux for 6 h, is allowed to return to room temperature, is partially concentrated and water and dichloromethane are added. The organic phase is separated off, is washed with water and is dried over sodium sulphate, the solvent is evaporated off and the residue is purified by chromatography on a column of silica gel. The oily product obtained crystallises from acetonitrile and is separated off by filtration, is rinsed with diethyl ether and is dried while heated under vacuum. 0.97 g of compound are finally isolated.

Melting point: 169.5°–170.5° C.

The table below illustrates the structures and physical properties of some compounds according to the invention.

TABLE

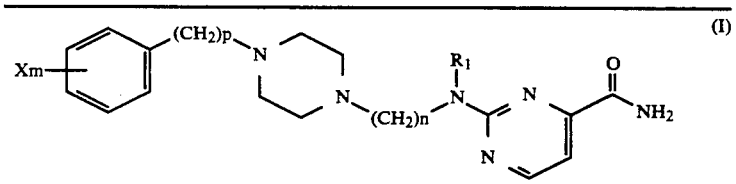

(I)

| N° | $X_m$ | n | p | $R_1$ | Salt/base | M(°C.) |
|---|---|---|---|---|---|---|
| 1 | H | 3 | 0 | H | fum. | 192–193 |
| 2 | H | 2 | 1 | H | 2fum. | 243–244 |
| 3 | H | 2 | 1 | $CH_3$ | 2fum. | 224–225 |
| 4 | H | 3 | 1 | H | 2fum. | 219–220.5 |
| 5 | 2-$OCH_3$ | 2 | 0 | H | fum. | 224–225 |
| 6 | 2-$OCH_3$ | 3 | 0 | H | ½fum. | 192.5–195 |
| 7 | 2-$OCH_3$ | 2 | 0 | $CH_3$ | fum. | 203–205 |
| 8 | 2-$OCH_3$ | 3 | 0 | $CH_3$ | base | 148.5–150.5 |
|   |   |   |   |   | 2HCl | 238–240 |
| 9 | 2-$cC_3H_5$ | 2 | 0 | H | fum.* | 207–210 |
| 10 | 2-$cC_3H_5$ | 3 | 0 | H | fum. | 196–198 |
| 11 | 2-$cC_3H_5$ | 2 | 0 | $CH_3$ | fum. | 177–180 |
| 12 | 2-$cC_3H_5$ | 3 | 0 | $CH_3$ | base | 169.5–170.5 |
|   |   |   |   |   | 2HCl | 225–227 |

TABLE-continued

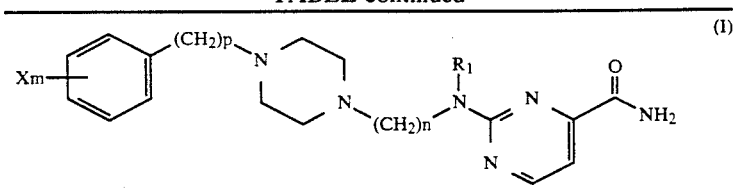

(I)

| N° | $X_m$ | n | p | $R_1$ | Salt/base | M(°C.) |
|---|---|---|---|---|---|---|
| 13 | 3-Cl | 2 | 0 | H | fum. | 227.5–228.5 |
| 14 | 3-Cl | 3 | 0 | H | fum. | 187–189 |
| 15 | 3-Cl | 4 | 0 | H | base | 136–138 |
|    |      |   |   |   | fum. | 155–160 |
| 16 | 3-Cl | 2 | 0 | $CH_3$ | fum. | 207–208 |
| 17 | 3-Cl | 3 | 0 | $CH_3$ | fum. | 190–192 |
| 18 | 2-$OCH_3$, 3-Cl | 3 | 0 | H | fum. | 196–198.5 |
| 19 | 2-$OCH_3$, 5-Cl | 3 | 0 | H | fum. | 211–212 |
| 20 | 2-$OCH_3$, 5-Cl | 2 | 0 | H | fum. | 222–223.5 |
| 21 | 2-$OCH_3$, 5-Cl | 2 | 0 | $CH_3$ | fum. | 174–175 |
| 22 | H | 3 | 0 | $CH_3$ | ½fum | 179–180 |
| 23 | 2-Cl | 3 | 0 | H | fum. | 190–192 |
| 24 | 2,5-$(OCH_3)_2$ | 3 | 0 | H | fum. | 158–160 |
| 25 | 2,4-$(OCH_3)_2$ | 3 | 0 | H | ½fum. | 169.5–171.5 |
| 26 | 2-$iC_3H_7$ | 3 | 0 | H | ½fum. | 215–217.5 |
| 27 | 2-$OCH_3$, 5-F | 3 | 0 | H | fum. | 202.5–205 |
| 28 | 3-Cl, 4-F | 3 | 0 | H | fum.* | 208–209.5 |
| 29 | 4-F | 3 | 0 | H | ½fum. | 185–187.5 |
| 30 | 2,4-$(OCH_3)_2$, 5-Cl | 3 | 0 | H | fum. | 177–179.5 |
| 31 | 3-Cl | 5 | 0 | H | ½fum. | 148–151 |

Note:
$iC_3H_5$ denotes the isopropyl group;
$cC_3H_5$ denotes the cyclopropyl group;
fum. denotes a fumarate;
fum.* denotes a fumarate hemihydrate;
½fum. denotes a hemifumarate;
2fum. denotes a difumarate;
2HCl denotes a dihydrochloride.

The compounds of the invention were subjected to a series of pharmacological tests which demonstrated their advantage as substances with therapeutic activities.

The antihypertensive activity of the compounds of the invention was studied in the spontaneously hypertensive rat.

Male rats aged approximately 10 months are placed for 20 min. in a chamber conditioned at 28° C. and 60% relative humidity, and their systolic arterial pressure and their cardiac frequency are measured by piezoelectric sensing of the pulse at the caudal artery. The stability of the arterial pressure is checked a number of times before the compounds are administered, the means of the last four pressure and frequency measurements then being taken as reference values.

The animals receive, subcutaneously, the solutions of the compounds under study in doses of 0.03 to 30 mg/kg, or only the solvent, and the arterial pressures and cardiac frequencies are measured 30 min, 1 h, 3 h and 5 h after the injection.

The minimum doses lowering the arterial pressure lie between 0.1 and 30 mg/kg.

The compounds of the invention have also formed the subject of studies relating to their antagonist activity for type $\alpha_1$ adrenergic receptors in the region of the low urinary apparatus. Their in-vitro activity was studied in the isolated rabbit urethra.

Adult rabbit urethra rings are prepared according to the method of Ueda et al., Eur. J. Pharmacol., (1984), 103, 249–254, and then, after sensitisation with noradrenalin, the concentration-phenylephrine response curve is determined in the absence and in the presence of the compound under study.

The $\alpha_1$-adrenergic antagonism power of each compound is evaluated by calculating $pA_2$, the antilogarithm of the molar concentration of antagonist in the presence of which the agonist concentration must be doubled to generate the same effect as in its absence.

The $pA_2$ values of the compounds are of the order of 5.5 to 9.

The in-vivo activity of the compounds of the invention was studied in relation to their effect on the urethral hypertonia generated by stimulation of the hypogastric nerve in the anaesthetised cat.

Adult male cats were anaesthetised with sodium pentobarbital and were prepared according to Theobald's method, J. Auton. Pharmac., (1983), 3, 235–239, in order to obtain a urethral hypertonia by stimulation of the sympathetic fibres of the hypogastric nerve. The contractile responses of the urethra to electrical stimulation of the hypogastric nerve are observed before and after intravenous administration of the compounds under study in cumulative doses of 1 to 1000 µg/kg.

The $\alpha_1$ adrenergic antagonism power of each compound is evaluated by calculating $ID_{50}$, the dose which inhibits the urethral hypertonia by 50%.

The $ID_{50}$ values of the compounds of the invention are of the order of 0.01 to 3 mg/kg.

The results of the tests show that the compounds of the invention have an antihypertensive activity. Furthermore, they show, in vitro, an antagonist activity of the $\alpha_1$ adrenergic receptors of the smooth muscles of the low urinary apparatus (urethra) when stimulated by an $\alpha_1$-adrenergic agonist (phenylephrine). In vivo they inhibit the urethral hypertonia generated by sympathetic nerve stimulation.

The compounds of the invention can therefore be employed for the treatment of cardiovascular disorders such as arterial hypertension. They can also be employed for the symptomatic treatment of diseases and disorders involving a hyperactivity of the α-adrenergic system in the region of the low urinary apparatus, and especially for the treatment of benign hypertrophy of the prostate, of dysuria and of pollakiuria.

The present invention provides a compound of formula (I) for use in a method of treatment of the human or animal body by therapy, in particular for use in a method of treatment of a cardiovascular disorder or disease or disorder involving a hyperactivity of the α-adrenergic system in the region of the urinary apparatus.

The present invention also provides the use of a compound of formula (I) in the manufacture of a medicament for the treatment of a cardiovascular disorder or disease or disorder involving a hyperactivity of the α-adrenergic system in the region of the urinary apparatus.

The present invention additionally provides a pharmaceutical composition comprising a compound of formula (I) and a pharmaceutically acceptable diluent or excipient.

The compositions may be presented in all suitable forms for enteral or parenteral administration, for example in the form of tablets, coated tablets, gelatin capsules, capsules, solutions or drinkable or injectable suspensions, or suppositories, being dosed so as to permit a daily dosage of 0.5 to 100 mg of active substance.

We claim:

1. A compound of formula (I)

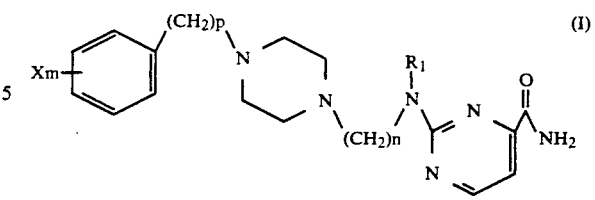

in which
n denotes 2, 3, 4 or 5,
p denotes 0 or 1,
$R_1$ denotes a hydrogen atom or a methyl group,
m denotes 0, 1, 2, 3, 4 or 5, and
each X, which may be identical or different to any other X if m is greater than 1, denotes fluorine, chlorine, methoxy, isopropyl or cyclopropyl,
in the form of a free base or an acid addition salt.

2. A compound according to claim 1 in which n denotes 2 or 3.

3. A compound according to claim 1 in which p denotes 0.

4. A compound according to claim 1 in which m denotes 0, 1 or 2.

5. A compound according to claim 1 which is in the form of a fumarate, fumarate hemihydrate, hemifumarate, difumarate or dihydrochloride salt.

6. A compound according to claim 1 in which m is 2.

7. A compound according to claim 6 in which X is in the 2- and 5-positions.

8. 2-[[3-[4-(5-chloro-2-methoxyphenyl)piperazin-1-yl]propyl]amino]pyrimidine-4-carboxamide or its acid addition salt.

9. A pharmaceutical composition comprising a pharmaceutically effective amount for treating urinary disorders of a compound as defined in claim 1 and a pharmaceutically acceptable diluent or excipient.

10. A method of treatment of a disease or disorder involving a hyperactivity of the α-adrenergic system in the region of the urinary apparatus, which method comprises administering an effective amount of a compound as defined in claim 1 to a subject suffering or liable to suffer from said disease or disorder.

* * * * *

UNITED STATES PATENT AND TRADEMARK OFFICE
CERTIFICATE OF CORRECTION

PATENT NO. : 5,164,397
DATED : November 17, 1992
INVENTOR(S) : Pascal GEORGE et al.

It is certified that error appears in the above-identified patent and that said Letters Patent is hereby corrected as shown below:

In column 1, line 65, "m denotes 1, 2, 3, 4 or 5" should be -- m denotes 0, 1, 2, 3, 4 or 5--.

In column 4, line 4, delete "3" and insert -- 2 --.

In column 4, line 4, delete "5-chloro-".

In column 4, line 5, delete "propyl" and insert --ethyl --.

Signed and Sealed this

Ninth Day of November, 1993

BRUCE LEHMAN

Attest:

Attesting Officer

Commissioner of Patents and Trademarks